(12) United States Patent
Spofforth

(10) Patent No.: US 8,414,541 B2
(45) Date of Patent: Apr. 9, 2013

(54) HYPODERMIC SYRINGE MECHANISM

(76) Inventor: Leonard Morris Spofforth, Wirral (GB)

( * ) Notice: Subject to any disclaimer, the term of this patent is extended or adjusted under 35 U.S.C. 154(b) by 0 days.

(21) Appl. No.: 11/885,239

(22) PCT Filed: Feb. 28, 2006

(86) PCT No.: PCT/GB2006/000727
§ 371 (c)(1),
(2), (4) Date: Jan. 4, 2008

(87) PCT Pub. No.: WO2006/090188
PCT Pub. Date: Aug. 31, 2006

(65) Prior Publication Data
US 2008/0140017 A1     Jun. 12, 2008

(30) Foreign Application Priority Data
Feb. 28, 2005 (GB) .................................. 0503990.4

(51) Int. Cl.
*A61M 5/00* (2006.01)
*A61M 5/24* (2006.01)
*A61M 5/28* (2006.01)
*A61M 5/315* (2006.01)

(52) U.S. Cl.
USPC ........... 604/232; 604/181; 604/187; 604/200; 604/201; 604/218; 604/233; 604/234; 604/235

(58) Field of Classification Search ................. 222/325, 222/326, 327; 604/110, 181, 187, 200, 201, 604/218, 232, 235, 244, 202, 233, 234; 128/919
See application file for complete search history.

(56) References Cited

U.S. PATENT DOCUMENTS

| | | | | |
|---|---|---|---|---|
| 1,574,579 A | * | 2/1926 | Jones | 604/234 |
| 3,076,455 A | * | 2/1963 | McConnaughey et al. | 604/232 |
| 3,144,178 A | * | 8/1964 | Sarnoff | 222/327 |
| 3,295,525 A | | 1/1967 | Evers et al. | |
| 3,430,627 A | * | 3/1969 | Kitaj | 604/240 |
| 3,556,099 A | * | 1/1971 | Knight et al. | 604/232 |
| 3,838,690 A | * | 10/1974 | Friedman | 604/232 |
| 3,848,593 A | * | 11/1974 | Baldwin | 604/206 |
| 4,585,445 A | * | 4/1986 | Hadtke | 604/234 |
| 4,871,094 A | * | 10/1989 | Gall et al. | 222/386 |
| 4,931,040 A | * | 6/1990 | Haber et al. | 604/110 |
| 5,078,698 A | | 1/1992 | Stiehl et al. | |

(Continued)

FOREIGN PATENT DOCUMENTS
WO     01/95960     12/2001

*Primary Examiner* — Kevin C Sirmons
*Assistant Examiner* — Shefali Patel
(74) *Attorney, Agent, or Firm* — James Creighton Wray

(57) ABSTRACT

An actuating mechanism for a hypodermic syringe comprises a flexible tongue (48) allowing the actuating mechanism to be bent to receive a cartridge (10) of injectant closed at its forward end with a septum (14) and at its rearward end with a slidable bung (18). The forward end of the cartridge (10) is fitted into a socket (36) wherein the tail (34*a*) of a hypodermic needle (34) pierces the septum (14) to access the injectant. With the cartridge (10) fitted, the tongue (48) is straightened, and a spring clip (50) holds the cartridge (10) in position. A plunger (38) can then be depressed, though a guide (42), to drive the bung (18) forward and make the injection. The cartridge (10), which may be a conventional cartridge of any kind, keeps the assembly rigid in use, and the whole assembly is disposed of after a single use, without dismantling.

11 Claims, 3 Drawing Sheets

U.S. PATENT DOCUMENTS

| | | | |
|---|---|---|---|
| 5,112,307 A * | 5/1992 | Haber et al. | 604/110 |
| 5,451,214 A * | 9/1995 | Hajishoreh | 604/235 |
| 6,080,456 A * | 6/2000 | Fonteyne | 428/35.7 |
| 7,338,477 B2 * | 3/2008 | Meyer et al. | 604/294 |
| 2003/0073958 A1 * | 4/2003 | Pond | 604/232 |
| 2004/0108339 A1 | 6/2004 | Hansen et al. | |

* cited by examiner

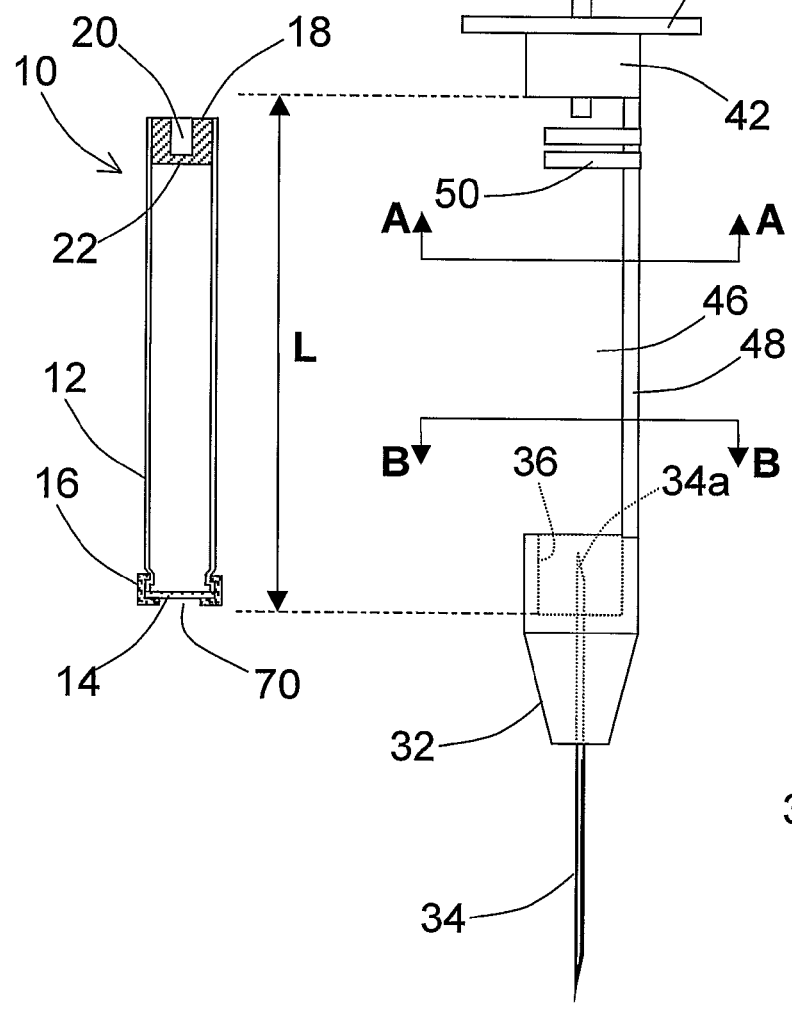
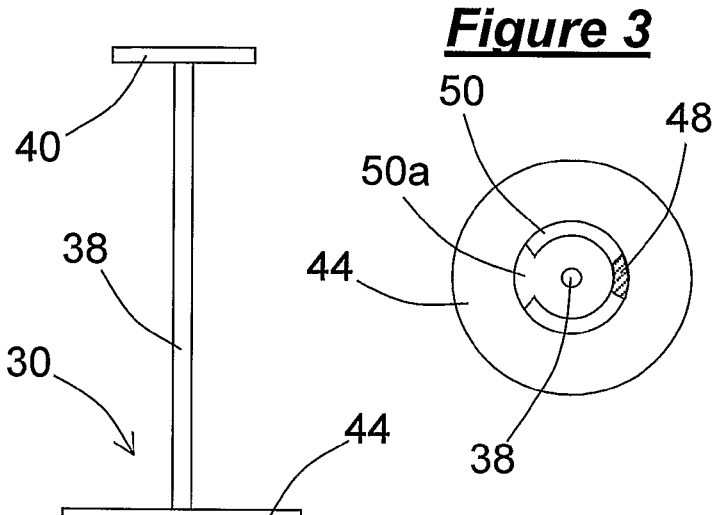
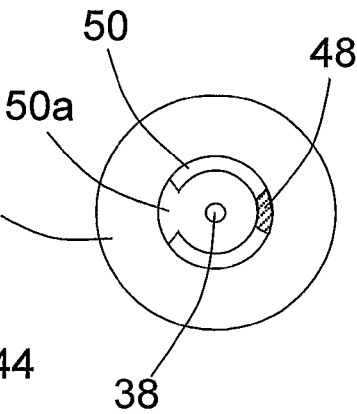
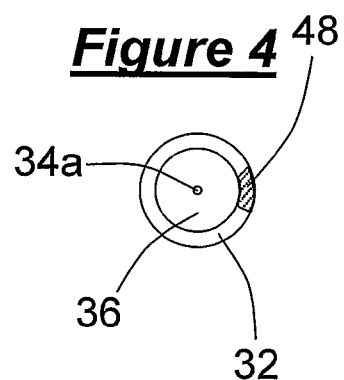

HYPODERMIC SYRINGE MECHANISM

This application claims the benefit of GB Application No. 0503990.4 filed Feb. 28, 2005 and PCT/GB2006/000727 filed Feb. 28, 2006, which are hereby incorporated by reference in their entirety.

FIELD OF THE INVENTION

This invention concerns hypodermic syringes particularly but not necessarily exclusively for administering dental local anaesthetics.

BACKGROUND OF THE INVENTION

For very many years, dental surgeons throughout the world have used a cartridge type of syringe to administer local anaesthetics. This type of syringe has a reusable actuating mechanism formed with a chamber into which is loaded a separate cartridge containing local anaesthetic agent—typically an amino-ester or an amino-amide mixed with a proportion of adrenaline. The cartridge has a slideable bung arranged to be engaged by a plunger of the actuating mechanism when the cartridge is in the chamber. After the cartridge has been loaded into the chamber a needle is attached to its forward end, usually by means of a screw thread arrangement. Then the practitioner can depress the plunger to drive the bung into the cartridge and expel the contents thereof to make an injection in the usual way. After use, the cartridge and needle are disassembled and disposed of, and the actuating mechanism sterilised for reuse.

A serious problem in this has emerged with the discovery that certain disease vectors—such as the prion proteins associated with variant Creutzfeldt Jakob disease (VCJD)—can survive conventional sterilisation. To counter this (and to provide certain other safety benefits) we have proposed the use of a wholly disposable syringe, in our international patent application PCT/GB01/02646, published as WO 01/95960.

SUMMARY OF THE INVENTION

Within international patent application PCT/GB01/02646 we disclose, among other things, a method of making a hypodermic syringe by adaptation of a conventional cartridge for dental local anaesthetic. It is an object of the present invention to provide, as an alternative to such adaptation, an actuating mechanism which can be disposed of with a spent cartridge after use.

Thus according to a first aspect of the invention there is provided an actuating mechanism for a hypodermic syringe of the cartridge type, which actuating mechanism includes an axially extending chamber that is at least in part flexibly deformable to receive a cartridge containing injectant and a plunger operable at a rearward end of the actuating mechanism to drive a slidable bung of the cartridge axially forwards thereinto and dispel the injectant, wherein the actuating mechanism has at its forward end a hub to mount a hypodermic needle and a socket extending rearwardly from the hub to receive the forward end of the cartridge.

The actuating mechanism preferably has a spring clip at the rearward end of the chamber to receive the rearward end of the cartridge.

Preferably the chamber of the actuating mechanism is configured and arranged so that when it is flexibly deformed the cartridge is inserted into the chamber forwardly, so that its forward end enters the socket, and sideways, so that its rear end enters the spring clip.

The chamber may include at least one tongue extending axially along a side of the chamber, which tongue is resiliently deformable sideways for the cartridge to be inserted into the chamber and thereafter positions the cartridge in the chamber in use.

Within the socket there may be a rearwardly directed nipple configured and arranged for mating engagement with the forward end of the cartridge.

A hypodermic needle may be mounted in the hub with a tip at its forward end for hypodermic intromission and a tail at its rearward end for penetrating the cartridge when inserted into the chamber. The needle is preferably bonded in the hub.

The actuating mechanism may be formed of synthetic plastics material.

It will now be understood that a syringe actuating mechanism according to the invention can be made very simply and cheaply and thus can be disposed of economically after a single use. This contrasts with previously known actuating mechanisms, the cost of which must be supported by repeated reuse. Those skilled in the practice of dentistry, especially, will also appreciate that each reuse requires sterilisation, which adds further to the cost of previous actuating mechanisms.

In a second aspect the invention extends to a hypodermic syringe including an actuating mechanism as set out above and a cartridge of injectant in the chamber of the actuating mechanism.

It will be well understood that a hypodermic injection could not be administered satisfactorily if the mechanism were able to deform in use, and therefore it is preferred that the cartridge is configured and arranged to resist deformation of the chamber. (This permits the use of standard cartridges, which are conventionally rigid).

Preferably the length of the chamber is a little greater than the length of the cartridge and the cartridge is longer than the length of the chamber less the depth of the socket.

The syringe may be included in apparatus for administering a hypodermic injection and comprising a sterile pack containing said actuating mechanism and instructions for assembling the cartridge with the actuating mechanism before use and instructions for disposing of the cartridge and the actuating mechanism without disassembly after a single use.

BRIEF DESCRIPTION OF THE DRAWINGS

Other features of the invention will be apparent from the following description, which is made by way of example only and with reference to the accompanying schematic drawings to an enlarged scale in which—

FIG. 1 shows in side elevation a conventional cartridge of injectable local anaesthetic for use in dentistry;

FIG. 2 shows in side elevation a syringe actuating mechanism, according to the invention, for injecting local anaesthetic from the cartridge of FIG. 1;

FIG. 3 is a transverse cross-section at A-A of FIG. 2, looking rearwards;

FIG. 4 is a transverse cross-section at B-B of FIG. 2, looking forwards;

DETAILED DESCRIPTION OF THE PREFERRED EMBODIMENTS

Figure 5:
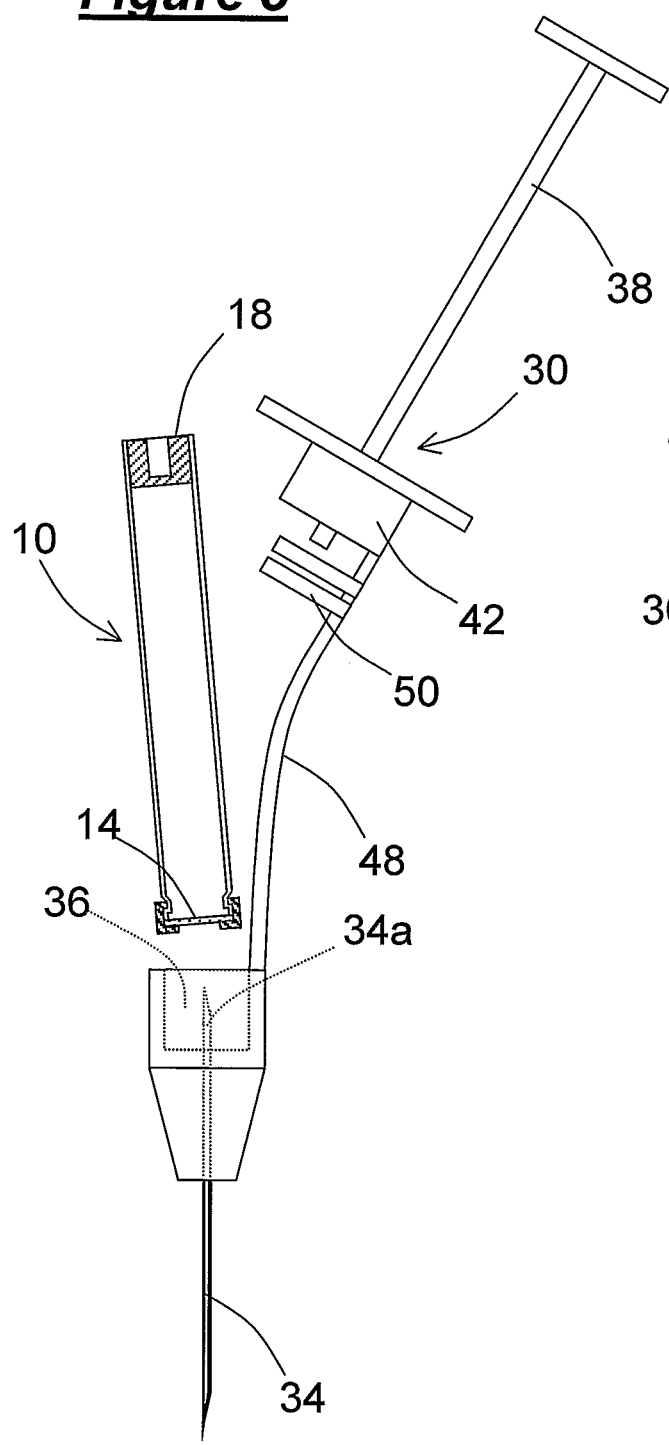
FIG. 5 shows in side elevation the cartridge of FIG. 1 being inserted into the actuating mechanism of FIG. 2.

Referring first to FIG. 1, this shows a conventional local anaesthetic cartridge indicated generally at 10. The cartridge 10 comprises an axially extending glass tube 12 which is substantially rigid. For simplicity the anaesthetic agent within the tube 12 is not shown in the drawing, but may be any of a range of agents such as amino-esters (eg procaine or tetracaine) or amino-amides (eg lidocaine, prilocaine or mepivacaine) possibly with a vasoconstrictor such as adrenaline or noradrenaline. Typically the tube 12 will contain between 1.0 and 2.2 ml of the anaesthetic agent. A preservative such as methylparaben and/or a spreading agent such as hyaluronidase may also be included. The tube 12 is closed at one, forward, end by a rubber septum 14 held in place by an aluminium cap 16. The rear end of the tube 12 is closed by a bung 18 formed with a recess 20. The periphery of the bung 18 sealingly engages the inner wall of the tube 12 to retain the anaesthetic in the tube 12 and, to make an injection, the bung 18 is driven into to tube 12 to dispel the anaesthetic therein, as will now be described in more detail.

To inject the local anaesthetic, the cartridge 10 may be loaded into a rigid chamber of a syringe actuating mechanism of the kind shown in U.S. Pat. No. 3,295,525, which is not shown herein but the general form of which is well known in dentistry. This actuating mechanism has at its rearward end a plunger formed with a nose arranged in use to extend into the recess 20 up to a resilient diaphragm 22 at the head of the bung 18 (that is, that part of the bung 18 which engages the injectant within the tube 12). At the forward end of the actuating mechanism is a means whereby a hypodermic needle is attached, such as a threaded dental needle attachment or Luer lock or the like, the action of which causes the tail of the needle to pierce the septum 14. The assembly is now ready for use in administering local anaesthetic to a patient. The tip of the needle is inserted hypodermically into the patient and the plunger is then slightly depressed to deflect the diaphragm 22 inwardly. The plunger is then released and the diaphragm resiles to effect aspiration. If aspiration is satisfactory the injection may proceed, and the practitioner presses the plunger further forward to cause a flange behind the nose to engage the bung and drive it into the cartridge 10 and inject the local anaesthetic.

Syringe actuating mechanisms broadly like that of U.S. Pat. No. 3,295,525 have been in use for many years. However they are costly (many times more expensive than the cartridge they operate, for instance) and their cost gives rise to compound problems. First, the actuating mechanism is much too expensive to be thrown away after a single use, and therefore needs to be sterilised after each use, which adds operating costs. Second, before being sterilised, the spent cartridge and, notably, the used needle have to be removed and disposed of, which exposes the practitioner to the risk of needle-stick and thereby transmission of disease from the patient. Third, the vectors of some very serious diseases—such as the prion proteins associated with VCJD—are now known to be resistant to regular sterilisation. And on top of all this, conventional actuating mechanisms are bulky, making them both disturbing to patients and awkward to use by practitioners with small hands. FIG. 2 shows an alternative actuating mechanism which is inexpensive, safe and convenient.

Thus referring now to FIG. 2, this shows an actuating mechanism indicated generally at 30. At the forward end of the actuating mechanism 30 is a hub 32 providing a mounting for a hypodermic needle 34. As indicated in broken lines, the needle 34 extends through the hub 32 so that its tail 32a extends into a socket 36 in the rear of the hub 32. (See also FIG. 4).

At the rearward end of the actuating mechanism 30 is a plunger 38. The plunger 38 is formed with a thumb piece 40 and extends through a guide 42 formed with a lateral finger piece 44. Between the hub 32 and the guide 42 is a chamber 46 bounded on one side by a tongue 48 and open on the other side to receive the cartridge 10 which as will be described in more detail below. As can be seen by comparing FIGS. 1 and 2, the axial length L of the chamber 46 is a little greater than that of the cartridge 10.

Towards the rearward end of the chamber 46 is a bifurcated spring clip 50 which, as shown in FIG. 3, has an arcuate cross-section to fit around a cartridge 10 inserted in the chamber 46, the cartridge 10 being sprung into position through an opening 50a in the spring clip 50. The tongue 48 and the spring clip 50 are integrally formed from resilient synthetic plastics material.

The resilience of the tongue 48 allows a cartridge 10 to be easily received in the actuating mechanism 30, as shown in FIG. 5. The tongue 48 is bent to one side to allow the forward end of the cartridge 10 to be fitted into the socket 36, wherein the tail 34a of the needle 34 pierces the septum 14. The tongue 48 is then straightened again so that the guide 42 comes over the bung 18 (it will be remembered that the chamber 46 is a little longer than the cartridge 10) and the rearward end of the cartridge 10 is sprung into the clip 50. To make the assembly ready for use, it is now necessary simply to move the plunger 38 forward to engage in the recess 20 of the bung 18.

Figure 6:
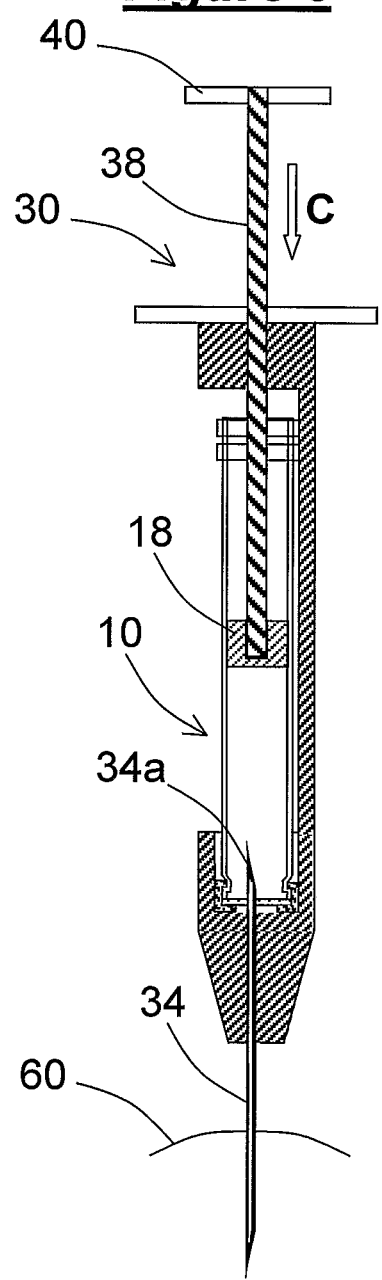
FIG. 6 shows in axial cross-section the actuating mechanism of FIG. 2 in use with the cartridge of FIG. 1.

The operation of the actuating mechanism is illustrated in FIG. 6. The practitioner first inserts the tip of the needle 34 hypodermically, eg in the gum 60 of a patient. Slight pressure on the thumb piece 40, followed by release, will effect aspiration. Then, subject to satisfactory aspiration, the plunger 38 can be advanced to complete the injection, as indicated by arrow C, local anaesthetic in the cartridge 10 being delivered by way of the needle 34, the tail 34a of which is within the cartridge 10. After the injection is complete (with any intermediate repositioning that may be required) the whole assembly is disposed of in a sharps bin, with no dismantling.

Figure 7:
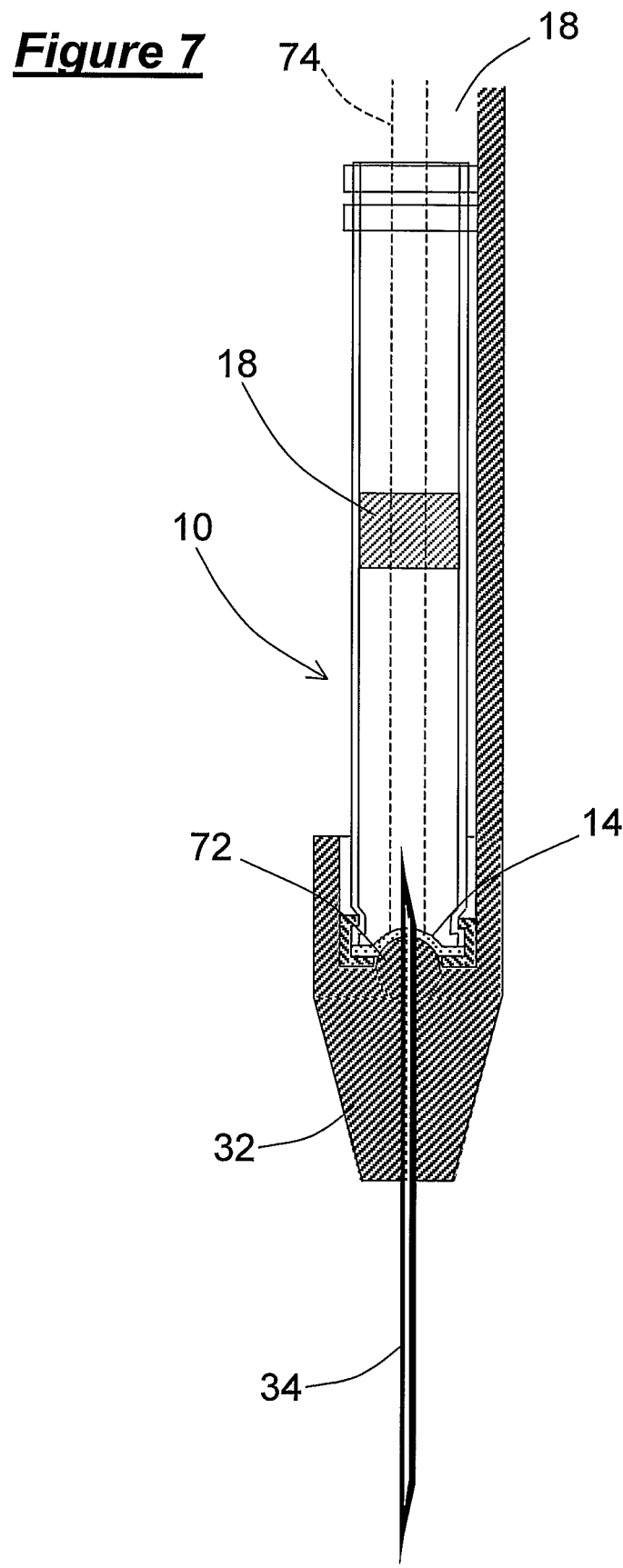
FIG. 7 is an enlarged cross-section showing a modification to the actuating mechanism of the invention.

FIG. 7 illustrates a modification of the invention as so far described. Referring back to FIG. 1 it will be noted that at the forward end of the cartridge 10 its tube 12 is closed by a rubber septum 14 held in place by an aluminium cap 16. The arrangement is such that the cartridge 10 thus has a forwardly facing recess 70 defined by the septum 14 and the cap 16. By the modification of FIG. 7, a rearwardly facing nipple 72 within the socket 36 is configured and arranged for mating engagement with the recess 70 of the cartridge 10. This provides additional support for the cartridge 10 in the chamber 46. This additional support is further enhanced by the fact that in use the septum 14 is tensioned across the nipple 72. Also, especially but not necessarily exclusively in the arrangement of FIG. 7, there may be two resiliently deformable tongues as indicated in broken lines at 74 instead of the single tongue aforedescribed.

Through simple plastic moulding, an actuating mechanism according to the invention can be made inexpensively enough to allow it to be disposed of with cartridge and needle after a single use. The Invention requires little in the way of material, and nor does it need to be rigid, since the cartridge itself provides the necessary rigidity in use. The operating cost of sterilisation is avoided, and immediate disposal after use greatly improves safety. Yet the invention can be used with conventional cartridges already approved for use and in large-scale manufacture.

Various additions and alterations will be apparent to those skilled in the science. For instance, the plunger 38 may be adapted to work with bungs of different forms that that shown herein. The needle 34 may be secured by means of a dental attachment or other means such as a Luer lock, which may be operated to cause the needle to penetrate the cartridge 10 after it has been fitted into the socket 36. Alternatively the needle may be pre-attached to the actuating mechanism, eg by bonding into place. Also, the actuating mechanism may be supplied in a sterile pack, with prescribing information as to its disposal.

The invention claimed is:

1. An actuating mechanism for a hypodermic syringe of a cartridge type, which actuating mechanism includes axially extending chamber to receive a cartridge containing injectant, a plunger operable at a rearward end of the actuating mechanism to drive a slidable bung of said cartridge in the chamber axially forwards into the cartridge and dispel the injectant therefrom, a hub at a forward end of the actuating mechanism to mount a hypodermic needle and a socket extending rearwardly from the hub to receive a forward end of the cartridge in use, wherein:

the cartridge is rigid relative to the chamber;
the chamber is at least in part flexible relative to the cartridge so that it can be deformed to admit the cartridge;
the cartridge and the chamber are relatively configured and arranged so that in use the cartridge cannot move in the chamber and therein its being rigid relative to the chamber resists flexing of the chamber; and
wherein the chamber includes at least one tongue extending axially along a side of the chamber, which tongue is flexible relative to the cartridge and resiliently deformable sideways to admit the cartridge into the chamber and thereafter engages the cartridge so as to position the cartridge in the chamber in use.

2. An actuating mechanism as claimed in claim 1, wherein the actuating mechanism has a spring clip at the rearward end of the chamber to receive a rearward end of the cartridge.

3. An actuating mechanism as claimed in claim 2, wherein the chamber is configured and arranged so that when it is flexibly deformed the cartridge is inserted into the chamber forwardly, so that its forward end enters the socket, and sideways, so that its rearward end enters the spring clip.

4. An actuating mechanism as claimed in claim 1, wherein within the socket there is a rearwardly directed nipple configured and arranged for mating engagement with the forward end of the cartridge.

5. An actuating mechanism as claimed in claim 1, wherein the hypodermic needle is mounted in the hub with a tip at its forward end for hypodermic intromission and a tail at its rearward end for penetrating the cartridge when inserted into the chamber.

6. An actuating mechanism as claimed in claim 5, wherein the needle is bonded in the hub.

7. An actuating mechanism as claimed in claim 1, wherein said chamber is integrally formed of synthetic plastics material.

8. A hypodermic syringe including the actuating mechanism as claimed in claim 1, and the cartridge containing the injectant in the chamber of the actuating mechanism.

9. A hypodermic syringe as claimed in claim 8, wherein a length of the chamber is a little greater than the length of the cartridge and the cartridge is longer than the length of the chamber less a depth of the socket.

10. An apparatus for administering a hypodermic injection, which apparatus comprises the hypodermic syringe as claimed in claim 8, a sterile pack containing said actuating mechanism, and instructions for assembling the cartridge with the actuating mechanism before use and instructions for disposing of the cartridge and the actuating mechanism without disassembly after a single use.

11. An actuating mechanism for a hypodermic syringe of a cartridge type, which actuating mechanism includes an axially extending chamber to receive a cartridge containing injectant, a plunger manually operable at a rearward end of the actuating mechanism to drive a slidable bung forwards into said cartridge in the chamber and dispel the injectant therefrom, a hub at a forward end of the actuating mechanism to mount a hypodermic needle and a socket extending rearwardly from the hub to receive a forward end of the cartridge in use, wherein:

the cartridge is not manually deformable;
the chamber is at least in part manually deformable to admit the cartridge without deformation of the cartridge;
the cartridge and the chamber are relatively configured and arrange so that in use the cartridge is a snug fit in the chamber and therein resists manual deformation of the chamber; and
wherein the chamber includes at least one tongue extending axially along a side of the chamber, which tongue is flexible relative to the cartridge and resiliently deformable sideways to admit the cartridge into the chamber and thereafter engages the cartridge so as to position the cartridge in the chamber in use.

* * * * *